United States Patent [19]

Konwitz

[11] Patent Number: 5,951,544
[45] Date of Patent: Sep. 14, 1999

[54] HANDPIECE ASSEMBLY FOR LASER APPARATUS

[75] Inventor: Ellie Konwitz, Ramat Gan, Israel

[73] Assignee: Laser Industries Ltd., Tel Aviv, Israel

[21] Appl. No.: 08/759,563

[22] Filed: Dec. 4, 1996

[51] Int. Cl.$^6$ .................................................. A61B 17/36
[52] U.S. Cl. ................................. 606/16; 606/13; 606/17
[58] Field of Search ...................................... 606/7, 15–16

[56] References Cited

U.S. PATENT DOCUMENTS

| | | |
|---|---|---|
| 3,467,098 | 9/1969 | Ayers . |
| 3,622,743 | 11/1971 | Muncheryan . |
| 3,821,510 | 6/1974 | Muncheryan . |
| 3,834,391 | 9/1974 | Block . |
| 4,538,609 | 9/1985 | Takenaka et al. . |
| 5,221,279 | 6/1993 | Cook et al. ................................. 606/15 |
| 5,304,172 | 4/1994 | Manoukian et al. ....................... 606/15 |
| 5,364,391 | 11/1994 | Konwitz ..................................... 606/16 |
| 5,374,266 | 12/1994 | Kataoka et al. ........................... 606/15 |

*Primary Examiner*—Max Hindenburg
*Assistant Examiner*—Roy D. Gibson
*Attorney, Agent, or Firm*—Friedman Siegelbaum LLP

[57] ABSTRACT

A handpiece assembly for laser apparatus is provided which includes a manually-graspable handpiece having a proximal end, a distal end, and a passageway through the handpiece from its proximal end to its distal end for receiving an optical fiber having a proximal end to be optically coupled to a laser beam source and a distal end to project through the distal end of the handpiece for delivering the laser beam to a working area; a clamping device for clamping the optical fiber to the handpiece such that a predetermined length of the optical fiber projects outwardly of the distal end of the handpiece; and an applicator device having at one end a quickly-attachable connector quickly attachable to and detachable from the distal end of the handpiece, and at the opposite end a rigid preformed sheath of a length to enclose the projecting length of the optical fiber, and of a shape to impart to the optical fiber a desired shape according to the particular working area to receive the laser beam.

10 Claims, 5 Drawing Sheets

HANDPIECE ASSEMBLY FOR LASER APPARATUS

FIELD OF INVENTION

The present invention relates to laser apparatus, and particularly to a handpiece assembly for laser apparatus such as used in laser surgery.

BACKGROUND OF THE INVENTION

Laser apparatus, widely used by surgeons for ablating or cutting tissue, generally includes a handpiece assembly manually-graspable by the surgeon for directing the laser beam to preselected working areas via an optical fiber at the distal end of the handpiece. The optical fiber is frequently enclosed within a bendable sheath which may be bent by the surgeon to a desired configuration according to the preselected working area to receive the laser energy. A serious problem in such handpieces, however, is that optical fibers are highly sensitive to stress fracture; that is, they are easily breakable if bent too sharply.

One way of solving this problem is to provide the apparatus with a plurality of interchangeable handpieces each having a desired curvature, enabling the surgeon to select the appropriate curved handpiece according to the configuration desired for a preselected working area. This solution, however, is very expensive since it requires a separate handpiece for each curvature. Moreover, it is also relatively inconvenient to the surgeon, since it may require realignment of the optical fiber in the handpiece with the laser beam delivery system at the proximal end of the handpiece for each removal of one handpiece and attachment of another in its stead.

A further drawback to this solution is the fact that stress fracture depends not only on the curvature forced on the fiber, but also on the time for which the fiber is forced to assume the curvature; therefore, holding the fiber at a particular curvature for a long period of time reduces the tightness of the curvature that the fiber is capable of assuming before stress fracture may occur.

SUMMARY OF THE PRESENT INVENTION

An object of the present invention is to provide a laser apparatus, and particularly a handpiece assembly therefore, having advantages in one or more of the above respects.

According to the present invention, there is provided laser apparatus, comprising: a manually-graspable handpiece having a proximal end, a distal end, and a passageway through the handpiece from its proximal end to its distal end for receiving an optical fiber having a proximal end to be optically coupled to a laser beam source and a distal end to project through the distal end of the handpiece for delivering the laser beam to a working area; a clamping device for clamping the optical fiber to the handpiece such that a predetermined length of the optical fiber projects outwardly of the distal end of the handpiece; and an applicator device having at one end a quickly-attachable connector quickly attachable to and detachable from the distal end of the handpiece, and at the opposite end a rigid preformed sheath of a length to enclose the projecting length of the optical fiber, and of a shape to impart to the optical fiber a desired shape according to the particular working area to receive the laser beam.

According to further features in the described preferred embodiment, there are a plurality of such applicator devices each having the same quickly-attachable connector at one end, but rigid preformed sheaths of different curvatures at the opposite end. The apparatus further includes a reference device having the same quickly-attachable connector at one end as the applicator devices, but a rigid preformed sheath at the opposite end constructed, e.g., as being closed at its outer tip, to locate the optical fiber at a predetermined location within the handpiece such as to fix the predetermined length of the optical fiber projecting outwardly of the distal end of the handpiece before the optical fiber clamped to the handpiece by the clamping device.

According to a further preferred feature, the handpiece further includes an outer bendable sheath effective to support the optical fiber according to the curvature of the rigid preformed sheath of the applicator device attached to the handpiece. In the described preferred embodiment, the inner bendable sheath is normally straight when in an unstressed condition, is bendable by low forces, and is elastic so that it returns to its straight condition when unstressed. Preferable, the bendable sheath is of "Tinel", a titanium-nickel alloy, As will be described below, such a handpiece assembly substantially reduces the danger of breaking the optical fiber by sharply banding the fiber, while at the same time it permits the optical fiber at the distal end to be configured according the particular working area selected (i.e., straight or with a predetermined curvature) for receiving the laser radiation, by merely substituting the appropriate applicator device having a preformed outer sheath according to the desired configuration. Removing one preformed sheath and attaching another is a much simpler operation than removing the complete handpiece assembly with the optical fiber, and reattaching another, since it does not require realignment of the optical fiber in the handpiece assembly with the laser beam delivery system at the proximal end of the handpiece assembly. Moreover, stocking a plurality of applicator devices with different preformed outer sheaths is considerably less expensive and more convenient than stocking a plurality of different complete handpiece assemblies.

In addition, such an apparatus permits the optical fibers to be stored in straight condition and to be curved by the preformed rigid sheath only at the time the applicator device for the rigid sheath only at the time the applicator device for the required curvature is applied to the handpiece. Such an arrangement permits the optical fibers to be curved to tighter curvatures before stress fracture may occur. When the optical fiber is enclosed within the bendable sheath, according to the preferred embodiment of the present invention, the optical fiber may actually be forced to assume a very tight curvature without causing stress fracture.

Further features and advantages of the invention will be apparent from the description below.

DETAILED DESCRIPTION OF THE DRAWINGS

The invention is herein described, by way of example only, with reference to the accompanying drawings, wherein.

DETAILED DESCRIPTION OF A PREFERRED EMBODIMENT

Figure 1:
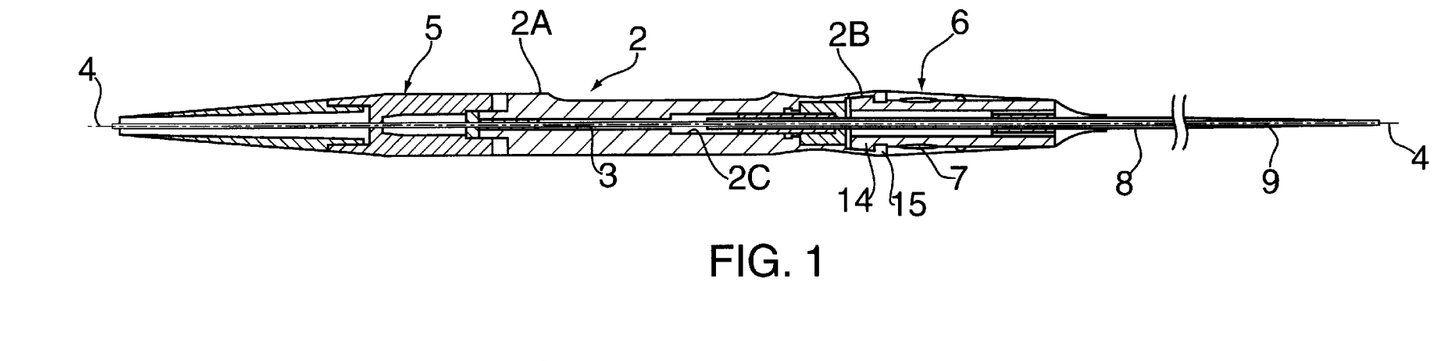
FIG. 1 is a longitudinal sectional view illustrating one form of handpiece assembly constructed in accordance with the present invention.

FIG. 1 illustrates a manually-graspable handpiece 2 having a proximal end 2a attachable to a source of laser energy for use by a surgeon in order to direct the laser energy through the distal end 2b of the handpiece to a preselected working area, e.g., for cutting or ablating tissue in the working area. For this purpose, the handpiece 2 includes a passageway 3 therethrough for receiving an optical fiber, schematically indicated at 4 in FIG. 1. A clamping device 5 is attached to the proximal end 2a of the handpiece 2 for fixing the optical fiber 4 to the handle such that a predetermined length of the optical fiber projects outwardly of the distal end 2b of the handpiece. An applicator device, generally designated 6 is attachable to the distal end 2b of handpiece 2 by means of a quickly-attachable connector 7 at one end of the applicator device. The opposite end of the applicator device includes a rigid preformed sheath 8 of a length to enclose the projected length of the optical fiber 4, and of a shape to impart to it a desired shape (e.g., straight or having a particular curvature) according to the particular working area to receive the laser beam.

The handpiece 2 further includes an inner bendable sheath 9 fixed within a passageway 3 of the handpiece projecting through the distal end 2b of the handpiece to enclose the length of the optical fiber 4 projecting through that end of the handpiece. Bendable sheath 9 is thus also enclosed by the rigid preformed sheath 8 of the applicator device 6 to support and protect the optical fiber during the application and removal of the applicator device.

A plurality of applicator devices 6 are provided, as shown in FIGS. 3a–3d, each having the same quickly-attachable connector 7 at one end and a different configuration of a rigid preformed sheath 8 at the opposite end. The surgeon may thus quickly adapt the handpiece for delivering the laser beam to any selected working area by merely detaching one applicator device and substituting therefore another application device of the appropriate rigid sheath configuration.

Figure 2:
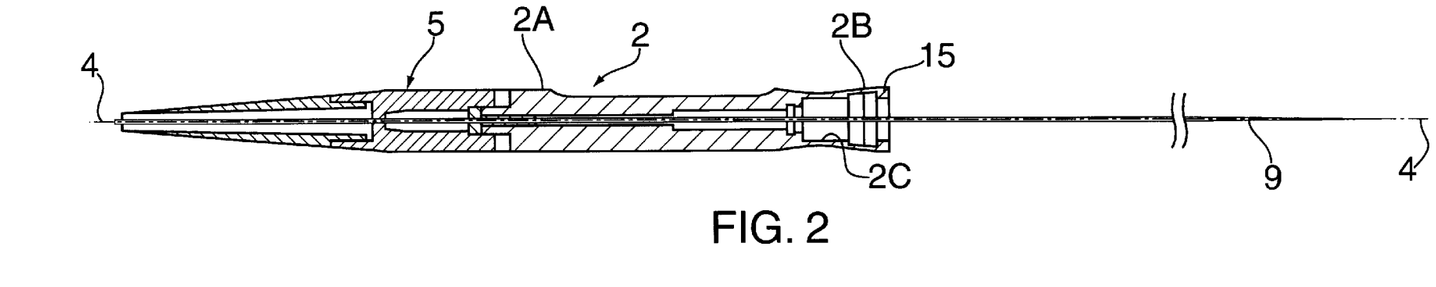
FIG. 2 is a sectional view more particularly illustrating the construction of the manually-graspable handpiece and the clamping device for clamping the optical fiber thereto.
Figures 3A, 3B:
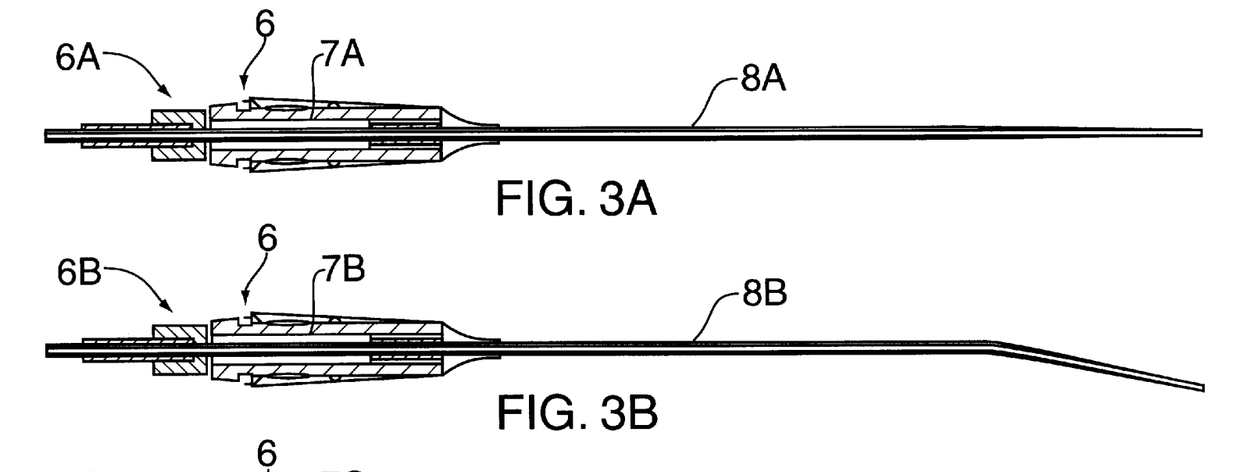
FIGS. 3a–3d are sectional views illustrating various types of applicator devices including rigid preformed sheaths of different curvatures which may be selectively attachable to the distal end of the handpiece of FIG. 2.
Figures 3C, 3D:
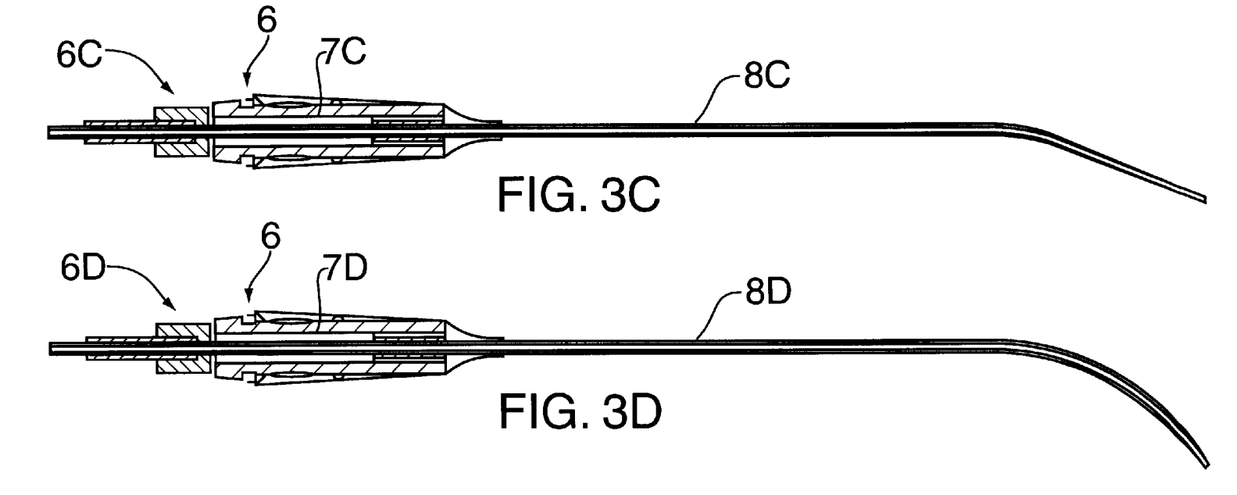
Figure 4:
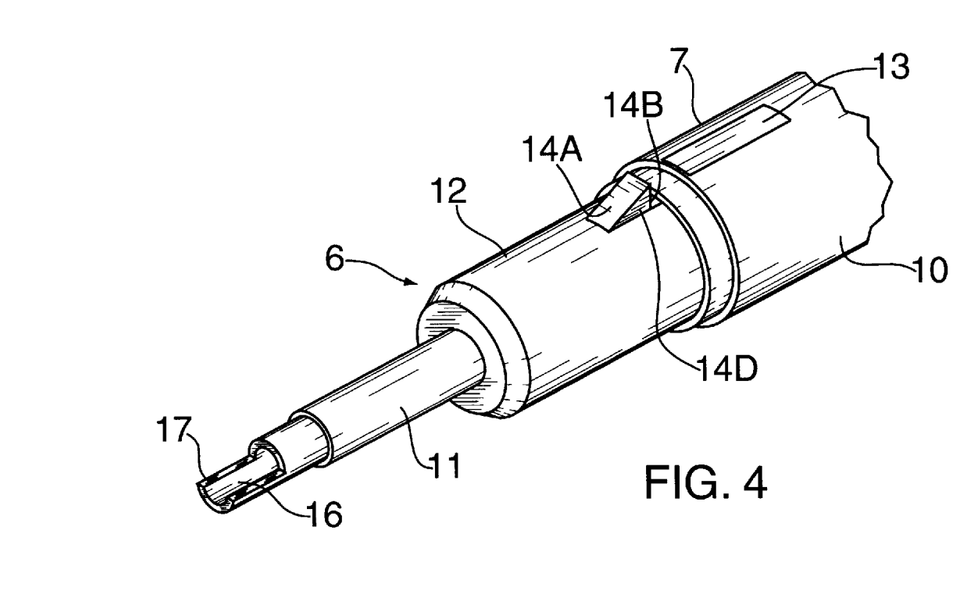
FIG. 4 is a three dimensional view illustrating the proximal end of the applicator device for receiving the optical fiber and for attachment to the distal end of the handpiece.

FIG. 2 illustrates the handpiece 2 and the clamping device 5 at its proximal end, but without the applicator device 6 at its distal end; whereas FIGS. 3a–3d illustrate examples of different types of applicator devices 6 which may be quickly attached to the handpiece 2. FIG. 4 illustrates the proximal end of to the applicator device 6 showing the structure enabling it to receive the distal end 2b of the handpiece and to be passed through the applicator device when attaching it to the handpiece.

The quickly-attachable connector 7 on each of the applicator devices 6 illustrated in FIGS. 3a–3d and in FIG. 4 include a cylindrical section 10 of relatively large diameter for grasping by the user, a tubular extension 11 at the opposite end of smaller diameter for insertion into the distal end 2b of the handpiece 2, and an intermediate cylindrical section 12 of smaller diameter than section 10 but of larger diameter than the tubular extension 11. The distal end 2b of handpiece 2 is formed with an axially-extending cavity 2c conforming to the external shape of the three sections 11, 12, 10, of connector 7 of the applicator device 6, for receiving that connector portion when the applicator device is inserted into the distal end of the handpiece.

Section 10 of connector 7 includes two diametrically-opposed buttons 13 joined to two diametrically-opposed locking elements 14 in section 12. Depression of the two buttons 13 by squeezing them together also depresses the looking elements 14 to a releasing position with respect to locking shoulders 15 (FIG. 2) in socket 2c at the distal end 2b of the handpiece.

As shown particularly in FIG. 4, the two locking elements 14 (only one of which is shown in FIG. 4) is formed with a slanted face 14a which permits the locking device to be quickly inserted into the distal end 2b of the handpiece 2, and a perpendicular locking face 14b engageable with the shoulders 15 in the handpiece to lock the applicator device therein when so inserted. In order to remove the applicator device, the two buttons 13 are manually depressed, to move their respective locking elements 14 inwardly to a released position with respect to the locking shoulders 15, thereby permitting the applicator device to be easily withdrawn from the handpiece.

The connector portion 7 of each applicator device 6 is formed with an axial bore passageway 16 for receiving the length of the optical fiber 4 projecting from the distal end 2b of the handpiece 2. To facilitate the insertion of the optical fiber into the passageway 16, the end of the tubular extension 11 facing the handpiece 2 is formed with a cutout 17 of substantially one-half the diameter of the tubular extension 11 and extending a short distance axially of that extension. Cutout 17 enables the user to conveniently enter the end of the optical fiber 4 projecting from handpiece 2 into passageway 16 from the side, and then to move the applicator device 6 into the cavity 2c of the handpiece 2 until the shoulders 15 of the handpiece engage locking surface 14d of the locking elements 14 to lock the applicator device in the handpiece. During this insertion of the applicator device, the projecting end of optical fiber 4 passes through passageway 16 in the connector section 7 of the applicator device 6, and then through the rigid preformed sheath 8 at the opposite end of the applicator device, which causes the respective length of the optical fiber to assume the configuration of the rigid sheath.

FIGS. 3a–3d illustrate examples of different configurations of rigid preformed sheaths that may be provided in the different applicator devices. Thus, the four applicator devices illustrated in FIGS. 3a–3d are identified by the reference numerals 6a–6d, respectively; their quickly-attachable connectors are identified as 7a–7d, identified as 8a–8d, respectively.

As indicated above, the connectors 7a–7d are of identical construction, whereas the rigid sheaths 8a–8d are of different configurations to enable the surgeon to apply a different configuration to the projecting length of the optical fiber according to the particular working area to receive the laser beam. Thus, rigid sheath 8a (FIG. 3a) is straight; rigid sheath 8b in FIG. 3b has a 15° curvature; rigid sheath 8c in FIG. 3c has a 30° curvature; and rigid sheath 8d in FIG. 3d has a 45° curvature.

Figure 5:
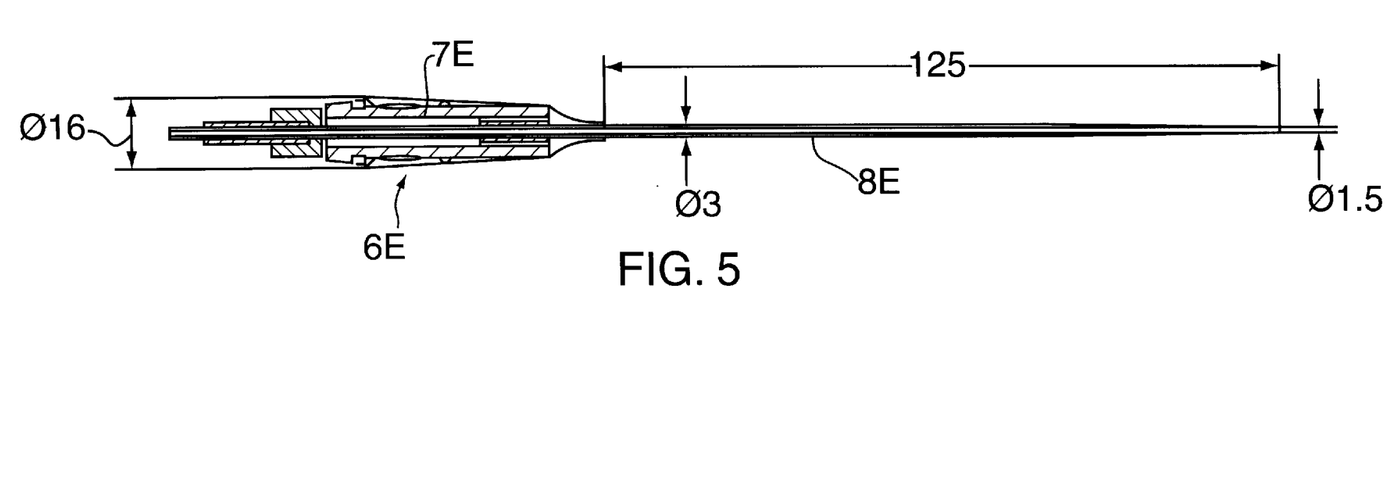
FIG. 5 illustrates a reference or jig device of similar construction as the applicator device of FIG. 4a, except that its rigid preformed sheath is closed at its outer tip to locate the optical fiber at a predetermined location within the handpiece before being fixed thereto.

The illustrated apparatus also includes a reference or jig applicator device shown in FIG. 5 and generally designated 6e. The reference applicator device 6e is of similar construction as applicator 6a illustrated in FIG. 3a, in that it includes a connector portion 7e identical to connector portion 7a in FIG. 3a, and a straight rigid sheath 8e the same as the straight rigid sheath 8a in FIG. 3a. In the reference applicator device of FIG. 5, however, the end of the rigid sheath 8e is closed by an end wall 18 (best seen in FIG. 6), rather than being open as in the rigid sheath 8a (as well as rigid sheaths 8b–8d of the other applicator devices illustrated in FIGS. 3b–3d respectively). The reference applicator device 6e, and particularly its closed end wall 18, is used for locating the optical fiber 4 at a precise location within the handle before the optical fiber is fixed to the handle by the clamping device 6, as will be described more particularly below.

Figure 6:
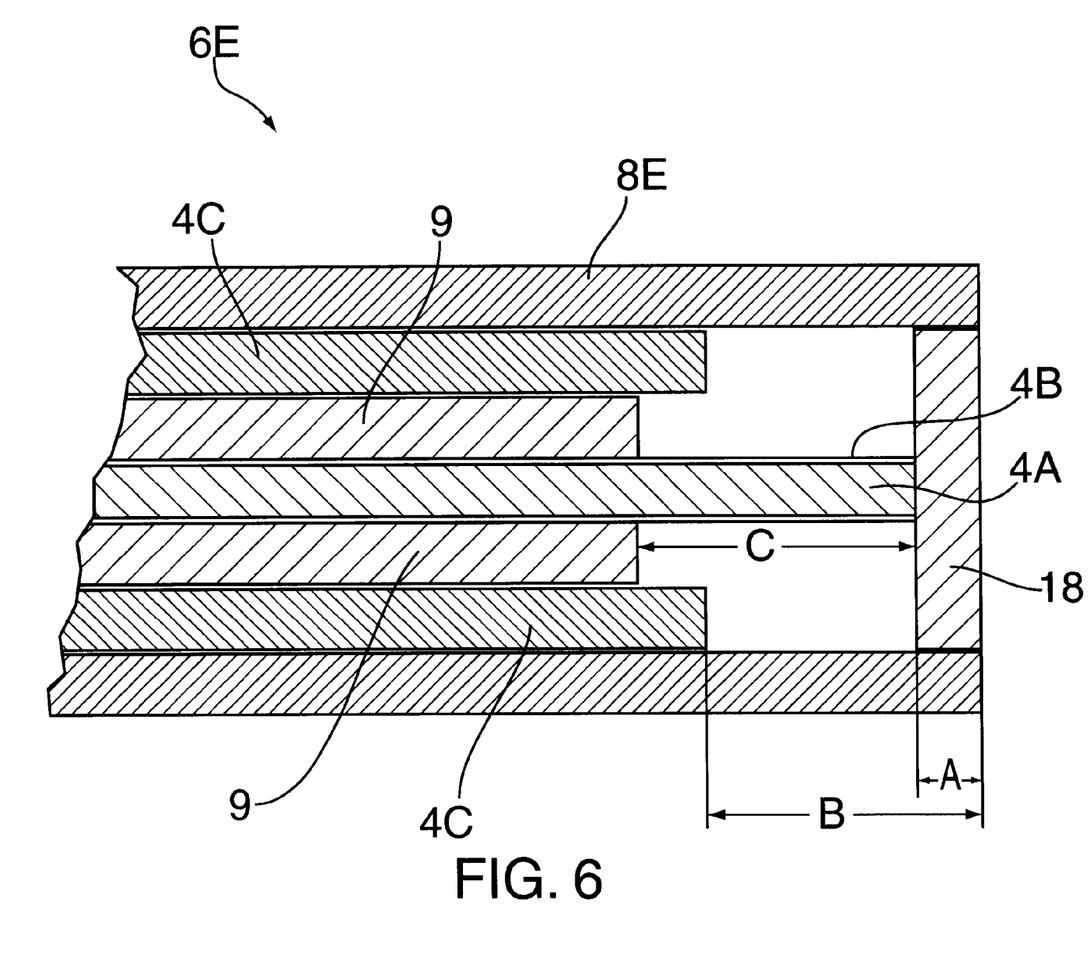
FIG. 6 is an enlarged sectional view of the outer tip of the reference device of FIG. 5 showing the manner in which it is used for precisely locating the optical fiber before fixing it to the handpiece.

The manner in which the reference applicator device 6e precisely locates the optical fiber 4 in the handpiece 2, before it is fixed therein by the clamping device 5, is more particularly illustrated in the enlarged sectional view of the end of the reference applicator device 6e in FIG. 6. In FIG. 6, the optical fiber, shown at 4, is of a conventional construction, including a core 4a of silica glass, a cladding 4b having a lower index of refraction than the core and an outer jacket 4c, serving as a buffer or protective layer for the core.

Also shown in FIG. 6 is the inner bendable sheath 9 effective to support the projecting portion of the optical fiber during the attachment and removal of one of the speculator devices 6a–6e. The inner bendable sheath 9 is fixed, as by gluing, within the handpiece 2, and is of a length so as to terminate slightly short from the outer tip of the optical fiber 4 as shown in FIG. 6. Bendable sheath 9 normally is straight when in an unstressed condition, is bendable by low forces, and is elastic so that it returns to its straight condition when unstressed. A preferred metal alloy that may be used for this purpose is "Tinel", which is a titanium-nickel alloy. The preformed outer rigid sheath may be of any suitable rigid material, a preferred material being stainless steel.

The distal tip of the optical fiber 4 is prepared as shown in FIG. 6. That is, the fiber cladding 4b extends flush with the tip of the fiber core 4a; the fiber jacket 4c terminates a short distance B from the tip of the fiber core 4a; and the inner bendable sheath 9 terminates a slightly larger distance C from the tip of the fiber core. A particularly important dimension is that shown at A in FIG. 6, namely the distance of the tip of the core 4a from the tip of the rigid preformed sheath 8, this distance being determined by the thickness of the end wall 18 of the preformed sheet 8e in the reference applicator device 6e.

The manner in which the reference applicator device 6e precisely locates the optical fiber 4 in the handpiece 2, before it is fixed therein by the clamping device 5 is described below. However, it will be helpful first to describe the construction and operation of the clamping device 6 to fix the fiber in the handpiece, as particularly illustrated in FIGS. 7 and 8.

Figure 7:
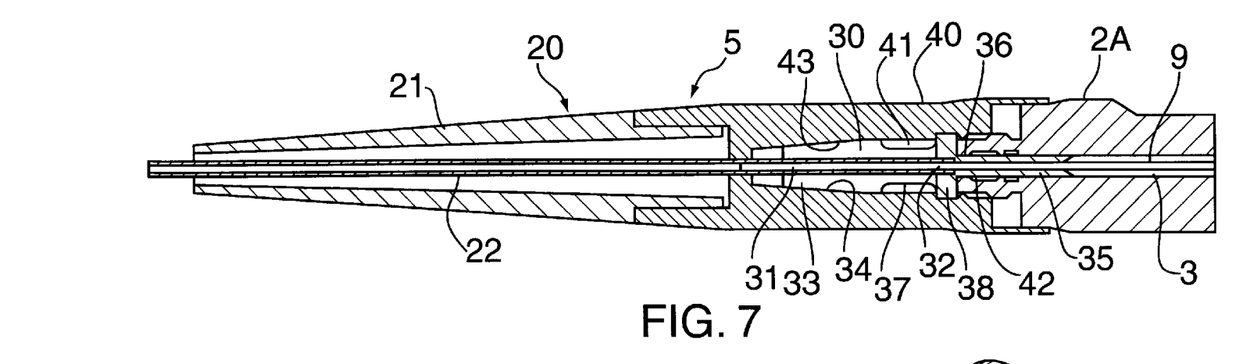
FIG. 7 is an enlarged sectional view illustrating the manner of fixing the optical fiber to the handpiece.
Figure 8:
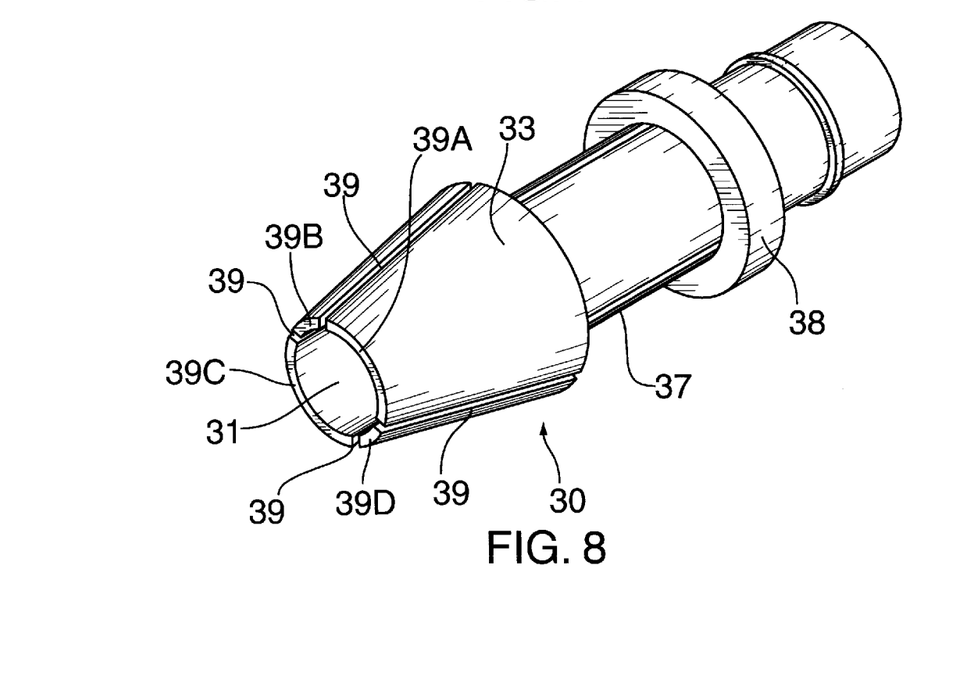
FIG. 8 is a three-dimensional view illustrating the clamping member used in fixing the optical fiber to the handpiece.

Clamping device 5 includes, at its proximal end, a strain relief sheath 21 of hard rubber or the like for preventing sharp bends in the optical fiber when received in that end of the clamping device, and also with a low-friction guiding sleeve 22, e.g., of soft silicone rubber or the like, for guiding the optical fiber when inserted into that end of the clamping device. Clamping device 5 further includes a clamping member 30 for clamping and releasing the optical fiber when passed though the handpiece 2 such that a predetermined length of the optical fiber projects outwardly of the distal end of the handpiece; and a manipulatable member 40 engaging clamping member 30 for moving it to a clamping position or to a releasing position.

Clamping member 30 is formed with a longitudinally-extending passageway 31 having an annular shoulder adjacent its distal end for receiving the inner guiding sheath 22 which limits against shoulder 32. The distal end of clamping member 30 includes an attaching section 35 of reduced diameter and formed with outer threads 36 for attaching the clamping device 5 to the proximal end 2a of the handpiece 2. The clamping section 33 and attaching section 35 are joined together by an intermediate section 37 and an abutting section 38 engageable with the proximal end of the handpiece 2 when attached thereto.

Clamping member 30 is further formed with four axially-extending circumferentially-spaced slits 39. Slits 39 start from the small-diameter tip of clamping member 30 and extend through its conical section 33 and its intermediate section 37, but not through the abutting section 38. These slits define four clamping jaws 39a–39d inwardly into clamping engagement with the inner flexible sheath 22, and the optical fiber therein, as will be described more particularly below.

The handpiece assembly illustrated in the drawings is used in the following manner:

First, clamping member 30 of clamping device 6 is attached to the proximal end of 2a of handpiece 2, by threading, via threads 38, attaching section 35 of the clamping member into passageway 3 of the handpiece, until the abutting section 38 of the clamping member abuts against the end o the handpiece. Manipulatable member 40, with the outer, stiff, strain-relief sheath 21 attached, is then applied, via its threads 42, to the proximal end of the handpiece while enclosing the clamping member 30, but is not yet tightened so that the jaws 39a–39d of the clamping member are in their open condition. The inner guiding sheath 22 is then inserted until its end engages shoulder 32. In this position of the guiding sheath 22, it becomes aligned with the respective end of the inner bendable sheath 9, which had been previously applied and fixed, e.g., by glue, in attaching section 35 of the clamping member 30.

After the clamping member 5 has thus been applied to the proximal end 2a of the handpiece 2, the reference applicator device 6e illustrated in FIG. 5, is applied to the distal end 2b of the handpiece 2. As described above, the reference applicator device 6e includes the same basic construction, namely a quickly-attachable connector 7e at one end for attachment to the distal end 2b of handpiece 2 and a rigid preformed sheath 8e to enclose the optical fiber, as the working applicator devices 6a–6d illustrated in FIGS. 3a–3d. However, in the reference applicator device 6e illustrated in FIG. 5, the tip of the rigid sheath 8e (FIG. 6) is closed by end wall 18. After the reference applicator 6e is applied, the optical fiber 4 is moved through it until end wall 18 is engaged by the tip of the optical fiber. This precisely fixes its position to produce a predetermined length of the optical fiber 4, and the inner bendable sheath 9, projecting outwardly of the distal end o the handpiece. Clamping device 5 is then manipulated to close jaws 39a–39d, and thereby to clamp in position the optical fiber with respect to the handpiece.

Before the optical fiber is inserted into the handpiece, its tip, e.g., the end 5 mm, is prepared as shown particularly in FIG. 6. Thus, the clad layer 4b extends to the tip of its core 4a so that both are spaced from the end of the outer sheath 8e by the distance A, namely the thickness of the end wall 18 of the outer sheath in the reference applicator device. The end of bendable sheath 9 is spaced by the distance B from the end of the preformed sheath 8e; and the end of jacket 4c of the optical fiber is spaced the distance C from the tip of the fiber core 4a and its clad 4b.

Distance A is significant since it determines the spacing of the tip of the optical fiber from the tissue to be tested by the laser beam. Distances B and C are significant only if the laser is provides with the inner bendable sheath 9, which is preferable but not essential. Thus, the distance B should not be too large so that the core may engage the bendable sheath 9 when inserting the core into the e bendable sheath and the applicator device, not too small such that the core may engage the outer sheath (8a–8e) of the applicator device when the core is inserted therethrough. Distance C should not be too large such that the core may engage and be broken by the rigid sheath during the insertion of the fiber or too small such that the clad will overheat and tend to melt during the application of laser energy to the working area.

As one example, the outer 5 mm of the elements illustrated in FIG. 6 may have the following dimensions: the outer diameter of sheath 8e may be 1 to 2 mm, preferable 1.5 mm; the inner diameter of sheath 8e may be 0.7 to 1.2 mm, preferably 0.9 mm; the thickness of its end wall 18 (and thereby distance A) may be 0.1 to 1.0 mm, preferably 0.5 mm; the outer diameter of clad layer 4b of the optical fiber may be 0.2 to 0.8 mm, preferably 0.4 mm; the outer diameter of the bendable sheath 9 may be 0.8 to 1.2 mm, preferably 1.0 mm; the outer diameter of the fiber jacket 4c may be 0.5 to 1.5 mm, preferably 0.75 mm; and the distance B may be 0.1 to 2.0 mm, preferably 1.0 mm; and the distance C may be 1.0 to 3.0 mm, preferably 1.5 mm.

After the reference applicator device 6e has been so applied, and the optical fiber 4 inserted into it until its tip engages wall 18 of that device, manipulatable member 40 of the clamping device 5 is then rotated in order to cause its conical clamping jaws 39a–39d to firmly clamp the optical fiber 4 within the inner flexible sheath 22, with a precise length of the optical fiber projecting outwardly of the distal end 2a of the handpiece. The reference applicator device 6e may then be removed, by merely squeezing its opposed buttons 13, to depress their locking elements 14. This permits the manual withdrawal of the reference applicator device from the handpiece 2, with the predetermined length of the optical fiber still projecting outwardly of the distal end 2b of the handpiece.

The appropriate working applicator device 6a–6d may now be applied having the required curvature for the particular working area. This is simply done by merely placing the tip of the optical fiber into the passageway 16 (FIG. 4) at the proximal end of the applicator device over the optical fiber 4, and its closed inner bendable sheath 9, until locking elements 14 of the applicator device snap behind the shoulders 15 at the distal end of the handpiece. When the selected applicator devices is so applied, the distances A, B and C (FIG. 6) are automatically maintained, and therefore no realignment is needed. Whenever a different curvature is desired for the distal tip of the optical fiber, it is only necessary to remove the applicator device, and reattach the appropriate one having the necessary curvature for the particular working area, both of which can be conveniently accomplished in a quick and facile manner, It will thus be seen that the handpiece assembly illustrated in the drawings enables the surgeon to quickly and conveniently apply the appropriate curvature to the working end of the optical fiber by merely removing and reattaching the appropriate applicator device. Such an arrangement thus substantially reduces the possibility of stress fracture, the expense of pre-stocking a plurality of complete handpiece assemblies, and also the need for realigning the optical fiber when another handpiece assembly is attached. In addition, the illustrated arrangement permits the optical fibers to be stored in a straight condition and to be curved, by the preformed rigid sheath, only at the time of use, thereby reducing the possibility of stress fracture even when tight curvatures are applied to the optical fiber.

While the invention has been described with respect to one preferred embodiment, it will be appreciated that this is set forth merely for the purposes of example, and that many variations may be made. For example, including the inner bendable sheath 9 has been found to provide a high degree of protection to the optical fiber when applying and removing the various applicator devices, and also to permit the optical fiber to be bent to relatively tight curvatures without danger of stress fracture. Nevertheless, in some cases this sheath may be omitted.

In addition, other means may be used for projecting a predetermined length of the optical fiber from the distal end of the handpiece, and for producing the various dimensional relationships at the distal tip of the fiber, e.g., as illustrated in FIG. 6. For example, the reference applicator device 8 could be open at its tip but merely shortened in length by the distance A (FIG. 6) so that a flat surface, such as the table, could be used for fixing the dimension A by merely providing the reference applicator device with a rigid sheath 8e which is open at its outer tip but of a length shorter than the rigid sheath of the working applicator devices by the distance A. Another alternative would be to make the reference applicator device in the form of a transparent tube having a marking to indicate dimension A to be aligned with the end of the optical fiber when inserted therein.

Other forms of quickly-attachable connectors may also be used for the applicator devices, such as the connector arrangement described above with respect to the fiber clamping device 5. Many other variations, modifications and applications of the invention will be apparent.

I claim:

1. Apparatus for delivering and directing light from a laser beam source, the apparatus comprising:

a) a manually graspable handpiece having a proximal end, a distal end, and a passageway through the handpiece from its proximal end to its distal end for receiving an optical fiber having a proximal end to be optically coupled to the laser beam source and a distal end to project through the distal end of the handpiece for delivering the laser beam to a working area;

b) a clamping device for clamping the optical fiber to the handpiece such that a predetermined length of the optical fiber projects outwardly of the distal end of the handpiece; and c) an applicator device having at one end a quickly-attachable connector quickly attachable to and detachable from the distal end of said handpiece, and at the opposite end a rigid preformed sheath of a length to enclose said projecting length of the optical fiber, and of a shape to impart to the optical fiber a desired shape according to the particular working area to receive the laser beam, and wherein there are a plurality of said applicator devices each having the same quickly-attachable connector at one end, but rigid preformed sheaths of different curvatures at the opposite end, further including a reference device having the same quickly-attachable connector at one end as the applicator devices, but a rigid preformed sheath at the opposite end constructed to locate the optical fiber at a predetermined location within the handpiece such as to fix the predetermined length of the optical fiber projecting outwardly of the distal end of the handpiece before the optical fiber is clamped to the handpiece by said clamping device.

2. The apparatus according to claim 1, wherein the rigid preformed sheath of said reference device is closed at its outer tip to locate the optical fiber at said predetermined location within the handpiece.

3. Apparatus for delivering and directing light from a laser beam source, the apparatus comprising:
   a) a manually graspable handpiece having a proximal end, a distal end, and a passageway through the handpiece from its proximal end to its distal end for receiving an optical fiber having a proximal end to be optically coupled to the laser beam source and a distal end to project through the distal end of the handpiece for delivering the laser beam to a working area;
   b) a clamping device for clamping the optical fiber to the handpiece such that a predetermined length of the optical fiber projects outwardly of the distal end of the handpiece; and
   c) an applicator device having at one end a quickly-attachable connector quickly attachable to and detachable from the distal end of said handpiece, and at the opposite end a rigid preformed sheath of a length to enclose said projecting length of the optical fiber, and of a shape to impart to the optical fiber a desired shape according to the particular working area to receive the laser beam,
   wherein said handpiece further includes an inner bendable sheath effective to support the optical fiber according to the curvature of the rigid preformed sheath of the applicator device attached to the handpiece.

4. The apparatus according to claim 3, wherein said inner bendable sheath is normally straight when in an unstressed condition, is bendable by low forces, and is elastic so that it returns to its straight condition when unstressed.

5. Apparatus for delivering and directing light from a laser beam source, the apparatus comprising:
   a) a manually graspable handpiece having a proximal end, a distal end, and a passageway through the handpiece from its proximal end to its distal end for receiving an optical fiber having a proximal end to be optically coupled to the laser beam source and a distal end to project through the distal end of the handpiece for delivering the laser beam to a working area;
   b) a clamping device for clamping the optical fiber to the handpiece such that a predetermined length of the optical fiber projects outwardly of the distal end of the handpiece; and
   c) an applicator device having at one end a quickly-attachable connector quickly attachable to and detachable from the distal end of said handpiece, and at the opposite end a rigid preformed sheath of a length to enclose said projecting length of the optical fiber, and of a shape to impart to the optical fiber a desired shape according to the particular working area to receive the laser beam,
   wherein said applicator device includes, at said quickly-attachable connector end thereof, a tubular extension having an end proximal to said applicator device and an end distal from said applicator device and a cylindrical passageway therethrough for receiving and guiding the optical fiber through the applicator device and its rigid preformed sheath, said distal end of said tubular extension being formed with a cutout leading to said cylindrical passageway and extending a short distance axially of the extension to facilitate the application of the optical fiber to said extension.

6. Apparatus for delivering and directing light from a laser beam source, the apparatus comprising:
   a) a manually graspable handpiece having a proximal end, a distal end having a locking shoulder, and a passageway through the handpiece from its proximal end to its distal end for receiving an optical fiber having a proximal end to be optically coupled to the laser beam source and a distal end to project through the distal end of the handpiece for delivering the laser beam to a working area;
   b) a clamping device for clamping the optical fiber to the handpiece such that a predetermined length of the optical fiber projects outwardly of the distal end of the handpiece; and
   c) an applicator device having at one end a quickly-attachable connector quickly attachable to and detachable from the distal end of said handpiece, and at the opposite end a rigid preformed sheath of a length to enclose said projecting length of optical fiber, and of a shape to impart to the optical fiber a desired shape according to the particular working area to receive the laser beam,
   wherein said quickly-attachable connector of the applicator device includes a spring-urged locking member having:
   a) a locking surface engageable with said locking shoulder in the distal end of the handpiece for locking the applicator device thereto, the locking member being in a released position when said locking surface is not engaged with said locking shoulder;
   b) an inclined surface engageable with the distal end of the handpiece for automatically clamping the locking member to permit its quick insertion into the distal end of the handpiece; and
   c) a button manually depressible to move said locking member to said released position, to permit quick manual withdrawal of the applicator device from said distal end of the handpiece.

7. Apparatus for delivering and directing light from a laser beam source, the apparatus comprising:
   a) a manually graspable handpiece having a proximal end, a distal end, and a passageway through the handpiece from its proximal end to its distal end for receiving an optical fiber having a proximal end to be optically coupled to the laser beam source and a distal end to project through the distal end of the handpiece for delivering the laser beam to a working area;
   b) a clamping device for clamping the optical fiber to the handpiece such that a predetermined length of the optical fiber projects outwardly of the distal end of the handpiece; and
   c) an applicator device having at one end a quickly-attachable connector quickly attachable to and detachable from the distal end of said handpiece, and at the opposite end a rigid preformed sheath of a length to enclose said projecting length of the optical fiber, and of a shape to impart to the optical fiber a desired shape according to the particular working area to receive the laser beam, wherein said clamping device for clamping the optical fiber to the proximal end of the handpiece includes a clamping member for clamping and releasing the optical fiber, and a manipulable member engaging said clamping member and manually movable to a clamping position to cause the clamping member to clamp; the optical fiber, or to a releasing position to cause the clamping member to release the optical fiber.

8. The apparatus according to claim 7, wherein said clamping member has a conical outer surface and said manipulable member has threads formed on it and said proximal end of the handpiece includes threads receiving the threads formed on said manipulable member such that the rotation of the latter member causes it to move axially off the handpiece, and said manipulable member further includes a conical inner surface engaging said conical outer surface on the clamping member to cause it to clamp the optical fiber when said manipulable member is rotated in one direction, and to release the optical fiber when the manipulable member is rotated in the opposite direction.

9. The apparatus according to claim 8, wherein said clamping member is formed with a passageway therethrough for receiving the optical fiber, and with a plurality of axially-extending circumferentially-spaced slits starting from its outer tip and terminating at an intermediate portion thereof, to define a plurality of clamping jaws radially displaceable to clamp and release the optical fiber upon the rotation of said manipulatable member.

10. The apparatus according to claim 9, wherein said clamping member includes an outer clamping section formed with said conical outer surface and with said slits, an inner attaching section for attaching the clamping member to the proximal end of the handpiece to position the clamping member therein with said conical section thereof projecting from the proximal end of the handpiece and enclosed by said manipulatable member.

* * * * *